(12) United States Patent
Kim et al.

(10) Patent No.: US 6,838,481 B1
(45) Date of Patent: Jan. 4, 2005

(54) SKIN WHITENER

(75) Inventors: Cheong-Taek Kim, Daejeon (KR);
Ho-Jeong Kim, Daejeon (KR);
Mu-Hyun Jin, Daejeon (KR);
Min-Hwan Jung, Daejeon (KR);
Jung-Mi Won, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 0 days.

(21) Appl. No.: 09/869,505

(22) PCT Filed: Dec. 14, 1999

(86) PCT No.: PCT/KR99/00768

§ 371 (c)(1),
(2), (4) Date: Jun. 28, 2001

(87) PCT Pub. No.: WO00/40543

PCT Pub. Date: Jul. 13, 2000

(30) Foreign Application Priority Data

Dec. 31, 1998 (KR) .......................................... 1998-63329
Jun. 1, 1999 (KR) ........................................... 1999-19970

(51) Int. Cl.$^7$ ............................................. C07C 69/76
(52) U.S. Cl. ...................................... 514/533; 560/107
(58) Field of Search ......................... 560/107; 514/533

(56) References Cited

U.S. PATENT DOCUMENTS 4,716,179 A 12/1987 Hecker et al. .............. 514/691

FOREIGN PATENT DOCUMENTS

| EP | 0 013 983 A2 | 8/1980 |
| JP | 08-175954 | 7/1996 |

OTHER PUBLICATIONS

"Structure of 7–Hydroxy–Lathyrol a Further Diterpene From Euphorbia Lathyris L.", Narayanan et al., Tetrahedron Letters No. 18, pp. 1325–1328, 1971.
"Constituents of Copper Spurge Seed (Lathyridis Seed) IV the Structure of Ester $L_3$", Ishiguro et al., Yakugaku Zasshi, vol. 95, No. 6, pp. 760–763, 1975.
"Acyloin Rearrangement in Alpha, Beta–Unsaturated Alpha–Ketols", Ishiguro et al., Tetrahedron Lett, vol. 5, pp. 315–318, 1975.
"Lathyrane Diterpenes From Euphorbia Lathyris", Itokawa et al., Phytochemistry, vol. 29, No. 6, pp. 2025–2026, 1990.
"Lathyrol–Benzoate–Diacetate From North American Euphorbia Esula Seeds (Euphorbiaceae)", Onwukaeme, et al., Ghana Journal of Chemistry 1(4) pp. 202–211, 1991.
"Jatrophane and Lathyrane Diterpenoid Esters From North American Leafy Spurge Seed", Onwukaeme et al., Phytochemistry, vol. 31, No. 10, pp. 3479–3482, 1992.
International Search Report in PCT/KR99/00768 dated Mar. 24, 2000.
International Preliminary Examination Report in PCT/KR99/00768 dated Aug. 30, 2000.

*Primary Examiner*—Johann Richter
*Assistant Examiner*—Paul A. Zucker
(74) *Attorney, Agent, or Firm*—Marshall, Gerstein & Borun LLP

(57) ABSTRACT

The invention relates to 5,15-diacetyl-3-benzoyllathyrol compound and a skin whitening composition containing the same. Since the composition of the invention contains 5,15-diacetyl-3-benzoyllathyrol as a melanine production inhibitor, it is excellent in inhibiting pigment stagnation and improving the discoloration of the skin or freckles. In addition, since it does not induce a secondary effect, it has excellent stability.

12 Claims, 3 Drawing Sheets

SKIN WHITENER

CROSS-REFERENCE TO RELATED APPLICATION

This is the U.S. national phase of International Application No. PCT/KR99/00768 filed Dec. 14, 1999, the entire disclosure of which is incorporated herein by reference.

BACKGROUND OF THE INVENTION (a) Field of the Invention

The present invention relates to a 5,15-diacetyl-3-benzoyllathyrol (EL-1) compound and a skin whitening composition comprising the same, and more particularly to a pharmaceutical and cosmetic composition comprising a 5,15-diacetyl-3-benzoyllathyrol (EL-1) compound which not only fades freckles and flecks, but can also be used as a skin whitener.

(b) Description of the Related Art

Having white and fine skin is many people's hope. Generally human skin color is determined hereditarily according to the concentration and distribution of melanin in the skin, but it can also be influenced by environmental or physiological conditions such as solar ultraviolet rays, fatigue, and stress. Melanin is produced through a non-enzymatic oxidation reaction after the enzyme tyrosinase acts on the amino acid tyrosine changing it into dopa and dopaquinone. While the process in which melanin is formed is known, the mechanism which induces melanin synthesis, or the step before the tyrosinase acts, is not yet understood in detail.

Therefore, conventional materials having tyrosinase inhibiting activities (such as hydroquinone, ascorbic acid, kojic acid, and glutathione) have been used after being mixed with ointments or cosmetics for skin whitening and freckle and fleck fading. However, hydroquinone has problems in that only an extremely restricted amount of it is used due to the severe skin irritation it causes, even though it's skin whitening effects are recognized. Ascorbic acid is easily oxidized, so cosmetics mixed with it have problems of color and odor changes; thiol based compounds such as glutathione, cysteine, etc. have unique unpleasant odors as well as problems in transdermal absorption; and glycosides and derivatives thereof have problems in that they cannot be appropriately used as mixed ingredients of cosmetics due to their high polarities.

Furthermore, although placenta extracts, etc. can be used in skin whitening compositions, these have problems such as insufficient whitening effects in clinical tests, among others. Therefore, existing skin whiteners are limited in their applications due to toxicity and stability problems.

SUMMARY OF THE INVENTION

This invention is made to solve the above problems. The object of the present invention is to provide a skin whitening composition which is safe for a living body, and has high melanin formation inhibiting effects and skin whitening effects.

The present invention provides a skin whitening composition comprising a 5,15-diacetyl-3-benzoyllathyrol (EL-1) compound of the following Chemical Formula 1, having high melanin formation inhibiting effects and skin whitening effects, in order to accomplish the above objective:

[Chemical Formula 1]

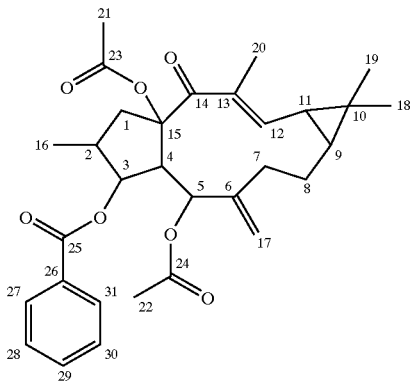

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

Figure 1:
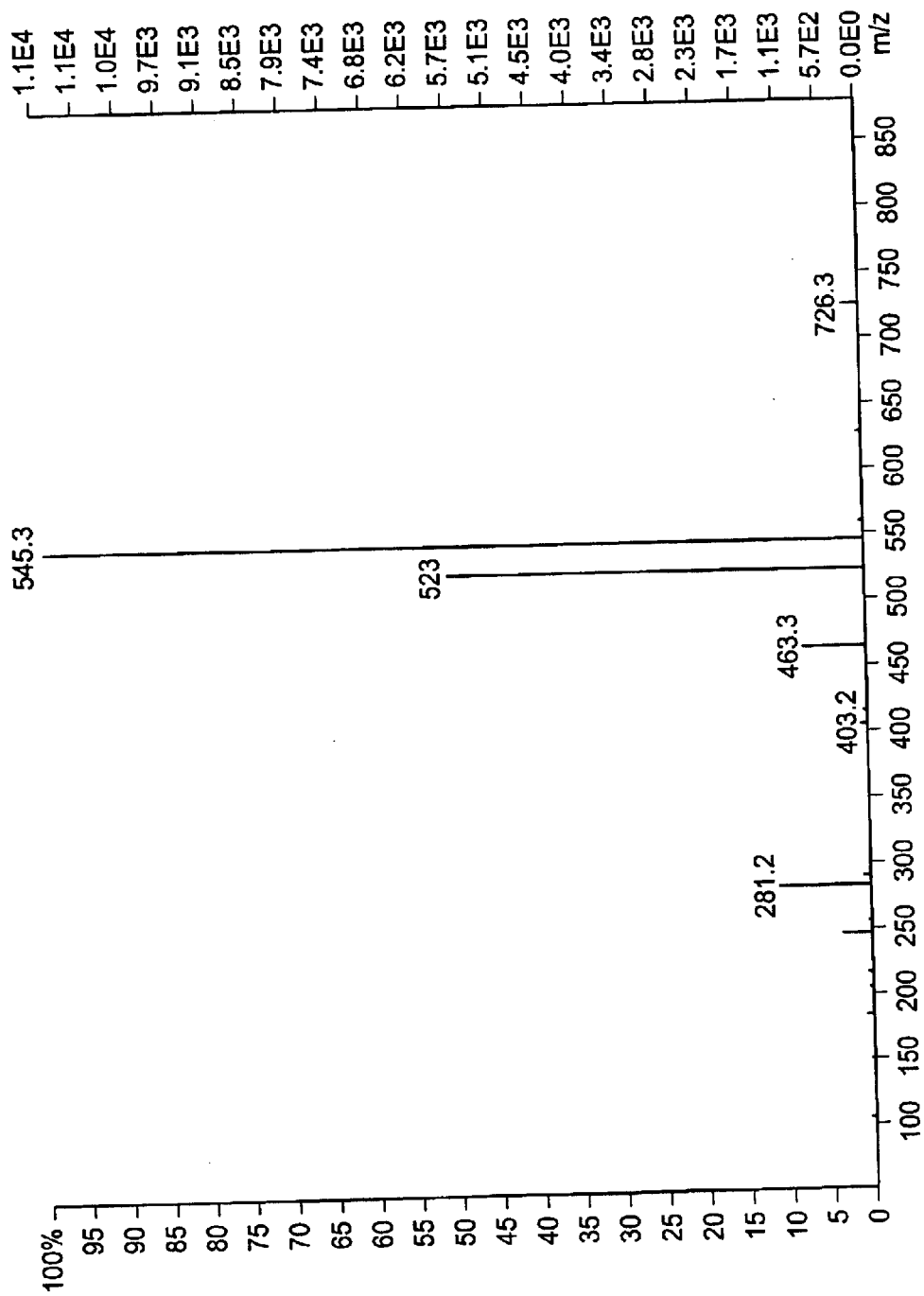
FIG. 1 is the mass spectrum of 5,15-diacetyl-3-benzoyllathyrol (EL-1)

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the drawings and description are to be regarded as illustrative in nature, and not restrictive.

The present invention is described in detail as follows.

The present inventors have completed the present invention by disclosing that 5,15-diacetyl-3-benzoyllathyrol (EL-1) has very strong melanin formation inhibiting effects and skin whitening effects. This determination was realized as a result of repeated studies on animals and plants which grow spontaneously in nature that were subjected to B16 mouse melanoma cells that are capable of screening even materials inhibiting melanin synthesis induction itself, in order to develop a new skin whitener.

*Euphorbia lathyris L.* is a biennial plant specimen, and seeds of *Euphorbia lathyris L.* were used in the present invention. It is disclosed in Dong-ui-bo-gam (a famous medical book written by Joon Huh during the Choun Dynasty (18$^{th}$ Century) quoted by Min-Gyo Dhin, Clinical Herbal Pharmacology, pp. 574–575 (1986)) that extracts of *Euphorbia lathyris L.* are effective on such symptoms as hydrops, epidemic dropsy, etc. Furthermore, although whitening effects of extracts of *Euphorbia lathyris L.* are disclosed in Japanese Patent No. 08175954, it is difficult to directly use the extracts as skin products or external use due to toxicities that bring about allergic reactions, for example (James A. Duke, Handbook of Medicinal Herbs, CRC Press, p. 189 (1985)).

A skin whitening composition of the present invention comprises a 5,15-diacetyl-3-benzoyllathyrol (EL-1) compound, and although there has been a paper published on structural isomers of 5,15-diacetyl-3-benzoyllathyrol (EL-1) in which an acetyl group is bonded at the No. 3 position and a benzoyl group is bonded at the No. 5 position (Japanese Pharmacy Magazine 95(6), 760–763, 1975), and a paper in which structures are not apparently identified, that is, a paper published without exact identification of derivatives of the No. 3 and No. 5 positions (Phytochemistry, 29(6), 2025–2026, 1990), with regard to the composition of the present invention compounds published in the conventional journals are clearly different from the present invention in that 5,15-diacetyl-3-benzoyllathyrol (EL-1) of the present invention has a benzoyl group bonded at the No. 3 position and an acetyl group bonded at the No. 5 position.

Therefore, 5,15-diacetyl-3-benzoyllathyrol (EL-1) of the present invention, as a type of lathyrane diterpene having a molecular formula of $C_{31}H_{38}O_7$, has never been isolated. EL-1 that exists in plants as well as EL-1 that is chemically synthesized can be used in the present invention. EL-1 of the present invention is contained in the plant *Euphorbia lathyris L*, and as it is also present in other plants in different amounts, the present invention is not limited to this plant.

In the present invention, EL-1 is purified from *Euphorbia lathyris L* extracts in which a large amount of EL-1 is contained, compared to other plants. In this purification process, although EL-1 is purified by column chromatography, high performance liquid chromatography, etc. using synthetic resins such as silica gel, active alumina, etc. after performing liquid-liquid extraction using solvents such as methanol, ethanol, propanol, isopropanol, butanol, acetone, ether, benzene, chloroform, hexane, cyclohexane, and petroleum ether, the purification methods are not limited to this.

Methods for extracting and purifying EL-1 of the present invention are described in detail as follows.

After *Euphorbia lathyris L*, which is commercially available as a botanical product, is purchased and crushed, the fragments are put into 5 to 20 volume % of water per dry weight of crushed fragments, and anhydrous or hydrous lower alcohol having 1 to 4 carbon atoms, or ethyl acetate, hexane, or chloroform is added, and boiled and extracted in an extractor with a reflux condenser at a temperature of from 50 to 100° C. for 1 to 5 hours. After filtering the extract with a 200 to 400 mesh filter cloth, the residues are extracted once more using the same method as above. After combining the extracted liquids and concentrating them under reduced pressure, the concentrate is freeze-dried or spray-dried, obtaining the dried extract. The dried extract of *Euphorbia lathyris L* is then suspended in water, the same volume of hexane is added, thereby obtaining oil phased hexane fractions.

Alternatively, after *Euphorbia lathyris L* is crushed, the fragments are compressed and filtered at a temperature range of from room temperature to 250° C., thereby obtaining an amount of oil of *Euphorbia lathyris L*.

Solvents are added to the obtained oil phased hexane fraction or the obtained compressed and filtered oil in an amount 0.2 to 10 times that of the amount of oil. The solvents can be ethanol, methanol, acetonitrile, purified water or a mixture thereof, they are added in a variety of ratios, and then liquid-liquid extracted thereby obtaining a solvent soluble fraction. EL-1 is separated from this fraction using column chromatography, and the separated EL-1 is again purified using high performance liquid chromatography. The structure of the separated purified material is analyzed by a mass spectrum and a nuclear magnetic resonance spectrum confirming that the purified material is EL-1.

It is confirmed from [molecular weight+H]$^+$ peak of 523 and [molecular weight+Na]$^+$ peak of 545.3 in the mass spectrum of FIG. 1 that the molecular weight of the purified material is 522.

Figure 2:
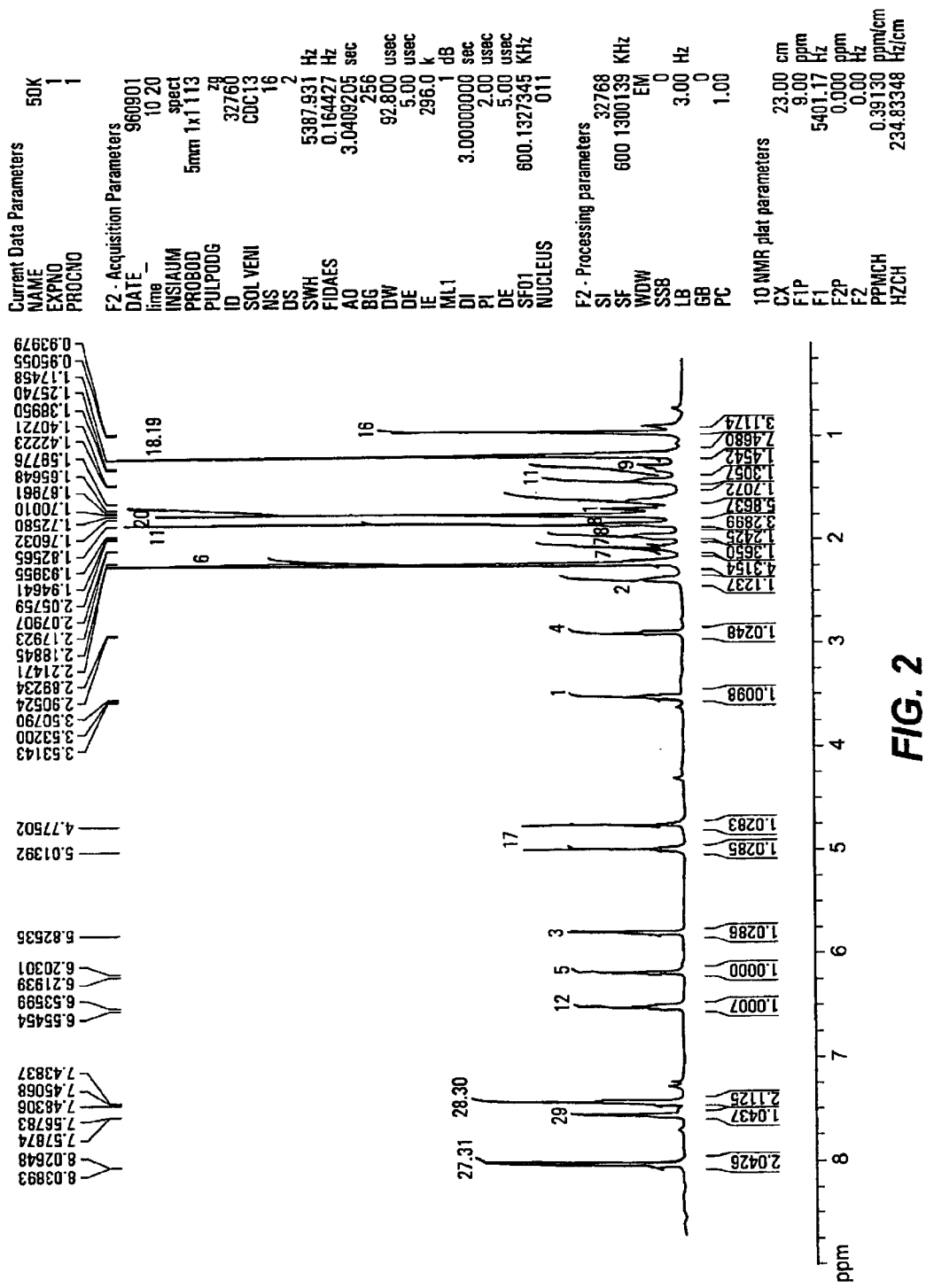
FIG. 2 is the proton magnetic resonance spectrum of 5,15-diacetyl-3-benzoyllathyrol (EL-1)

FIG. 2 shows the results in which peaks of 5.82 (dd)ppm and 6.21(d)ppm are identified as a No. 3 hydrogen peak and a No. 5 hydrogen peak respectively of the above Chemical Formula 1 in the proton magnetic resonance spectrum, and peak identifications of FIG. 2 are 1-H: 3.52(m), 1.70(m), 2-H: 2.35(m), 3-H: 5.82(dd), 4-H: 2.90(dd), 5-H: 6.21(d), 7-H: 2.10(m), 2.06(m), 8-H: 1.94(m), 1.75(m), 9-H: 1.26 (m), 11-H: 1.41(dd), 12-H: 6.54(d), 16-H: 0.94(d), 17-H: 5.01(s), 4.78(s), 18-H: 1.17(s), 19-H: 1.17(s), 20-H: 1.72(s), 21-H: 2.21(s), 22-H: 1.83(s), 27-H: 8.03(d), 28-H: 7.45(t), 29-H: 7.57(t), 30-H: 7.45(t), and 31-H: 8.03(d).

Figure 3:
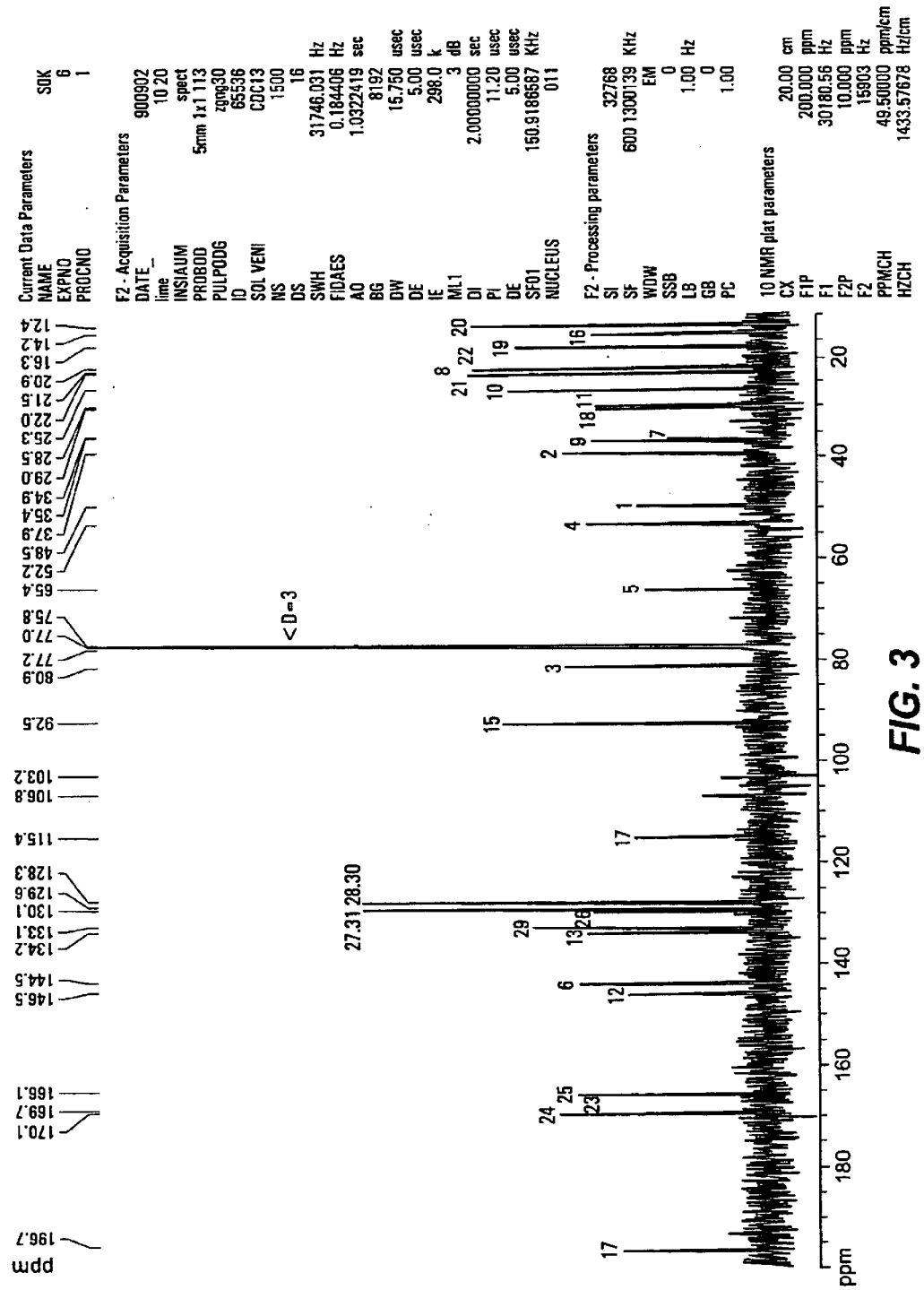
FIG. 3 is the carbon magnetic resonance spectrum of 5,15-diacetyl-3-benzoyllathyrol (EL-1).

FIG. 3 shows the results in which peaks of 80.9 ppm and 65.4 ppm are identified as No. 3 and No. 5 carbon peaks respectively in the carbon magnetic resonance spectrum, and peak identifications of FIG. 3 are C: 48.5, 2-C: 37.9, 3-C: 80.8, 4-C: 52.2, 5-C: 65.4, 6-C: 144.5, 7-C: 34.9, 8-C: 21.6, 9-C: 35.4, 10-C: 25.3, 11-C: 28.5, 12-C: 146.5, 13-C: 134.2, 14-C: 196.7, 15-C: 92.5, 16-C: 14.2, 17-C: 115.4, 18-C: 29.0, 19-C: 16.8, 20-C: 12.4, 21-C: 22.0, 22-C: 20.9, 23-C: 169.7, 24-C: 170.1, 25-C: 166.1, 26-C: 130.1, 27-C: 129.6, 28-C: 128.3, 29-C: 133.1, 30-C: 128.3, and 31-C: 129.6.

When mouse B-16 melanoma cells are treated with an *Euphorbia lathyris L* extract prepared in this process, i.e., EL-1, a very strong melanin synthesis inhibiting effect is shown. Additionally, when this compound is put in various cosmetic materials such as an external skin ointment or lotion and applied to human skin, the skin whitening effect is excellent. Furthermore other side effects are not shown, so EL-1 is seen to be an improved, safe and very effective agent for freckle or fleck fading, and for skin whitening.

The dry content of EL-1 in external-use skin ointments or cosmetics is from 0.00001 to 10 weight %, preferably from 0.001 to 1 weight %. The clear skin whitening effect is not expected when the content is below 0.00001 weight %, and conspicuous improvements in effect are not observed when the content is increased to over 10 weight %.

EXAMPLES and COMPARATIVE EXAMPLES are described in order to help understand the present invention. However, the following EXAMPLES are only for easily understanding the present invention, and the present invention is not limited to the following EXAMPLES.

EXAMPLE 1

100 g of the crushed fragments of *Euphorbia lathyris L*. were put into 500 ml of an 80% methanol solution and boiled in a reflux extractor with a cooling condenser for about 3 hours, after which it was extracted and then filtered with 300 mesh filter cloth. The residue was then processed once more with the same method as above. The extracted liquids were combined, filtered with Whatman No. 2 filter paper, and insoluble materials were removed at room temperature. The liquid was then concentrated at 60° C. under reduced pressure in distillation equipment with a cooling condenser, and the concentrate was suspended in 300 ml of purified water. 300 ml of hexane were added, the mixture was shaken well, and hexane soluble material was obtained. 450 mg of the fraction containing effective constituents were obtained by chromatographing this hexane soluble material with silica gel column. This fraction was again purified by high performance liquid chromatography, and 350 mg of EL-1 was isolated.

EXAMPLE 2

After *Euphorbia lathyris L.* was purchased and 100 g of crushed fragments of *Euphorbia lathyris L.* were compressed and filtered at room temperature, thus obtaining 35 ml of oil of *Euphorbia lathyris L.* An ethanol fraction was obtained by adding 35 ml of ethanol to the above obtained oil and liquid-liquid extracting the mixture. 300 mg of the fraction containing effective constituents were obtained by chromatographing this ethanol fraction with a silica gel column. This fraction was again purified by high performance liquid chromatography, and 200 mg of EL-1 were isolated.

EXAMPLE 3

340 mg of EL-1 were obtained by performing the extraction in the same process as in EXAMPLE 1 except that 500 ml of 100% ethanol solution were used as a extracting solvent.

EXAMPLE 4

300 mg of EL-1 were obtained by performing the extraction in the same process as in EXAMPLE 1 except that 500 ml of 99.9% chloroform solution were used as a extracting solvent.

EXAMPLE 5

310 mg of EL-1 were obtained by performing the extraction in the same process as in EXAMPLE 1 except that 500 ml of 99.9% n-hexane solution were used as a extracting solvent.

EXAMPLE 6

After *Euphorbia lathyris L.* was purchased and crushed, 100 ml of 80% ethanol solution were added to 35 ml of oil of *Euphorbia lathyris L.* obtained in the same process as in EXAMPLE 2, 230 mg of the fraction containing effective constituents were obtained by chromatographing the ethanol fraction obtained by the liquid-liquid extraction, with a silica gel column. The fraction was again purified by high performance liquid chromatography, and 170 mg of EL-1 were separated.

EXAMPLE 7

After *Euphorbia lathyris L.* was purchased and crushed, 100 g of the crushed fragments were compressed and filtered at 150° C. thus obtaining 40 ml of oil. An acetonitrile fraction was obtained by adding 200 ml of 90% acetonitrile to the above obtained oil and liquid-liquid extracting the mixture. 470 mg of the fraction containing effective constituents were obtained by chromatographing this acetonitrile fraction with a silica gel column. This fraction was again purified by high performance liquid chromatography and 340 mg of EL-1 were isolated.

TEST EXAMPLE 1

Test of Melanin Formation Inhibiting Effects of EL-1 at the Cellular Level

The whitening effect was tested at the cellular level by adding EL-1 obtained from the above EXAMPLES 1 to 7 to a cultured solution of B-16 mouse melanoma cells (Lotan R., Lotan D. Cancer Res. 40:3345–3350, 1980) as follows.

The EL-1 obtained in EXAMPLES 1 to 7 was added to a culture solution of B-16 mouse melanoma cells so that the final concentrations become 1 µg/ml, 5 µg/ml and 50 µg/ml respectively, and they were cultured for 3 days. After trypsin was added to the cells and the solution was removed from the culture container and centrifuged, melanin was extracted. 1 ml of sodium hydroxide solution (1 N concentration) was added to the extracted melanin and boiled for about 10 minutes to dissolve the melanin. The test was carried out in a way whereby the formed melanin amount was represented in absorbance per unit cell number, expressed as $A_{400}/10^6$ cells by measuring the absorbance at 400 nm. After repeating this test 3 times, the melanin formation amount relative to the control was calculated as an inhibition ratio (%) using the average values.

TABLE 1

| Samples | Melanin formation amount | Inhibition ratio (%) |
|---|---|---|
| Control (no addition) | 0.044 ± 0.004 | — |
| EL-1 (final conc. 1 µg/ml) | 0.032 ± 0.001 | 28 |
| EL-1 (final conc. 5 µg/ml) | 0.019 ± 0.003 | 57 |
| EL-1 (final conc. 50 µg/ml) | 0.007 ± 0.001 | 85 |
| Hydroquinone (final conc. 1 µg/ml) | 0.025 ± 0.002 | 43 |
| Hydroquinone (final conc. 10 µg/ml) | Cell extinction | |

Note:
repetition number = 3

As shown in the above Table 1, it can be seen that EL-1 obtained according to EXAMPLES has an equal melanin formation inhibition capability on cultured mouse melanoma cells when compared with a conventionally known whitening material hydroquinone. Furthermore, hydroquinone has a strong melanin formation inhibition capability at low concentration, but it cannot be tested over 10 µg/ml of concentration due to its high cell toxicity. EL-1, on the other hand, does not show cell toxicity even at the concentration of 50 µg/ml and has a higher melanin formation inhibiting effect than hydroquinone. Therefore, the present invention can be very usefull in terms of freckle and fleck fading as well as for it's skin whitening effects.

PREPARATION EXAMPLE 1 AND COMPARATIVE EXAMPLE 1

A skin ointment for external use was prepared by mixing respective constituents represented in the following Table 2 in the ratios represented as in the following Table 2, wherein EL-1 was obtained from the respective EXAMPLES 1 to 7.

TABLE 2

| | Weight % | |
|---|---|---|
| Compositions | PREPARATION EXAMPLE 1 | COMPARATIVE EXAMPLE 1 |
| El-1 | 0.01 | — |
| Diethyl sebecate | 8 | 8 |
| Spermaceti | 5 | 5 |
| Polyoxyethylene oleylether phosphate | 6 | 6 |
| Sodium benzoate | Appropriate quantity | Appropriate quantity |
| Petrolatum | Balance* | Balance* |

Note:
*is an amount which makes total 100 weight %.

PREPARATION EXAMPLE 2 AND COMPARATIVE EXAMPLE 2

A cosmetic cream was prepared by mixing respective constituents represented in the following Table 3 in the ratios represented as in the following Table 3, wherein EL-1 was obtained from the respective EXAMPLES 1 to 7.

TABLE 3

| Compositions | PREPARATION EXAMPLE 2 (weight %) | COMPARATIVE EXAMPLE 2 (weight %) |
|---|---|---|
| EL-1 | 0.01 | — |
| Stearic acid | 1.0 | 1.0 |
| Cetanol | 2.0 | 2.0 |
| PEG-20 sorbitan monostearate | 1.0 | 1.0 |
| Sorbitan monostearate | 1.0 | 1.0 |
| Mineral oil | 10.0 | 10.0 |
| Trioctanoate | 5.0 | 5.0 |
| Triethanolamine | 0.5 | 0.5 |
| Carbomer | 0.2 | 0.2 |
| Glycerin | 5.0 | 5.0 |
| Propyleneglycol | 3.0 | 3.0 |
| Antiseptic | Appropriate quantity | Appropriate quantity |
| Incense | Appropriate quantity | Appropriate quantity |
| Purified water | Balance* | Balance* |

Note:
*is an amount which makes total 100 weight %.

PREPARATION EXAMPLE 3 and COMPARATIVE EXAMPLE 3

A cosmetic soft toilet water (lotion) was prepared by mixing respective constituents represented in the following Table 4 in the ratios represented as in the following Table 4, wherein EL-1 was obtained from the respective EXAMPLES 1 to 7.

TABLE 4

| | Weight % | |
|---|---|---|
| Compositions | PREPARATION EXAMPLE 3 | COMPARATIVE EXAMPLE 3 |
| El-1 | 0.01 | — |
| Ethanol | 10.0 | 10.0 |
| Hydrogenated caster oil (POE40) | 1.0 | 1.0 |
| Methyl paraoxybenzoate | 2.0 | 2.0 |
| Glycerin | 5.0 | 5.0 |
| 1,3-butyleneglycol | 6.0 | 6.0 |
| Incense | Appropriate quantity | Appropriate quantity |
| Pigment | Appropriate quantity | Appropriate quantity |
| Purified water | Balance* | Balance* |

Note:
*is an amount which makes total 100 weight %.

PREPARATION EXAMPLE 4 and COMPARATIVE EXAMPLE 4

A cosmetic essence was prepared by mixing respective constituents represented in the following Table 5 in the ratios represented as in the following Table 5, wherein EL-1 was obtained from the respective EXAMPLES 1 to 7.

TABLE 5

| | Weight % | |
|---|---|---|
| Compositions | PREPARATION EXAMPLE 4 | COMPARATIVE EXAMPLE 4 |
| El-1 | 0.01 | — |
| Propyleneglycol | 10.0 | 10.0 |
| Glycerin | 10.0 | 10.0 |
| Sodium hyaturonate (1%) | 5.0 | 15.0 |
| Ethanol | 5.0 | 5.0 |
| Hydrogenated caster oil (POE40) | 1.0 | 1.0 |
| Methyl paraoxybenzoate | 0.1 | 0.1 |
| Carbomer | 0.3 | 0.3 |
| Triethanolamine | 0.4 | 0.4 |
| Incense | Appropriate quantity | Appropriate quantity |
| Purified water | Balance* | Balance* |

Note:
*is an amount which makes total 100 weight %.

PREPARATION EXAMPLE 5 and COMPARATIVE EXAMPLE 5

A cosmetic facial pack was prepared by mixing respective constituents represented in the following Table 6 in the ratios represented as in the following Table 6, wherein EL-1 was obtained from the respective is EXAMPLES 1 to 7.

TABLE 6

| | Weight % | |
|---|---|---|
| Compositions | PREPARATION EXAMPLE 5 | COMPARATIVE EXAMPLE 5 |
| El-1 | 0.01 | — |
| Glycerin | 5.0 | 5.0 |
| Propyleneglycol | 4.0 | 4.0 |
| Polyvinylalcohol | 15.0 | 15.0 |
| Ethanol | 8.0 | 8.0 |
| Hydrogenated caster oil (POE40) | 1.0 | 1.0 |
| Poloxyethylene (10) oleyl ether | 1.0 | 1.0 |
| Methyl paraoxybenzoate | 0.2 | 0.2 |
| Incense | Appropriate quantity | Appropriate quantity |
| Pigment | Appropriate quantity | Appropriate quantity |
| Purified water | Balance* | Balance* |

Note:
*is an amount which makes total 100 weight %.

PREPARATION EXAMPLE 6 and COMPARATIVE EXAMPLE 6

A cosmetic nutritive toilet water (lotion) was prepared by mixing respective constituents represented in the following Table 7 in the ratios represented as in the following Table 7, wherein EL-1 was obtained from the respective EXAMPLES 1 to 7.

TABLE 7

| | Weight % | |
|---|---|---|
| Compositions | PREPARATION EXAMPLE 6 | COMPARATIVE EXAMPLE 6 |
| EL-1 | 0.01 | — |
| Hydrogenated caster oil (POE40) | 1.0 | 1.0 |
| Methyl paraoxybenzoate | Appropriate quantity | Appropriate quantity |
| Glycerin | 6.0 | 6.0 |
| 1,3-butyleneglycol | 5.0 | 5.0 |
| Carbomer | 0.2 | 0.2 |
| Triethanolamine | 0.3 | 0.3 |

TABLE 7-continued

| Compositions | Weight % | |
|---|---|---|
| | PREPARATION EXAMPLE 6 | COMPARATIVE EXAMPLE 6 |
| Propyleneglycol | 5.0 | 5.0 |
| Ethanol | 2 | 3.2 |
| Carboxyvinylpolymer | 1 | 0.1 |
| Pigment | Appropriate quantity | Appropriate quantity |
| Incense | Appropriate quantity | Appropriate quantity |
| Purified water | Balance* | Balance* |

Note:
*is an amount which makes total 100 weight %.

TEST EXAMPLE 2

A group of 20 subjects comprised of healthy men and women were selected for irradiation with a 1,000 watt ORIEL solar simulator. Prior to irradiation, aluminum foil masks, with 7 millimeter (mm) diameter holes arranged in two rows of 6 holes each, covered the lower parts of both arms. The arms were irradiated from a distance of 10 centimeters (cm) at an intensity of 60 milliJoules per square centimeter. Samples containing and not containing EL-1 prepared according to PREPARATION EXAMPLES 1 to 6 and COMPARATIVE EXAMPLES 1 to 6 were coated on the skin of the test subjects at the sites of their designated respective holes in pairs. This coating was applied two times per day, starting from three days before commencing the irradiation, and continued for three weeks after the irradiation. (Note that the facial pack formulations of PREPARATION EXAMPLE 5 and COMPARATIVE EXAMPLE 5 were detached 15 minutes after application.)

The degree of pigment deposition for the PREPARATION EXAMPLES and the COMPARATIVE EXAMPLES hole sites was determined by visual observation with the naked eye. The results of determination were represented in the following Table 8.

TABLE 8

| Test materials | Clearly effective (subjects) | Effective (subjects) | No difference (subjects) |
|---|---|---|---|
| PREPARATION EXAMPLE 1 | 7* | 7 | 6 |
| PREPARATION EXAMPLE 2 | 2 | 10 | 8 |
| PREPARATION EXAMPLE 3 | 1 | 9 | 10 |
| PREPARATION EXAMPLE 4 | 2 | 9 | 9 |
| PREPARATION EXAMPLE 5 | 3 | 8 | 9 |
| PREPARATION EXAMPLE 6 | 3 | 9 | 8 |

Note:
*means number of subjects

As shown in the above Table 8, whitening ointment and cosmetic materials containing EL-1 prepared according to PREPARATION EXAMPLES 1 to 6 showed whitening effects for at least 10 of the 20 subjects. Especially in the comparison test of PREPARATION EXAMPLE 1 and COMPARATIVE EXAMPLE 1, in which a large amount of EL-1 was applied, 35% showed evident pigment deposition inhibiting effects, and no negative side effects in the skin were detected. Therefore it can be seen that EL-1 is safe and a very effective and improved agent for fading freckles and flecks, or for skin whitening.

A skin whitening composition comprising EL-1 of the present invention not only has merits in that it can be mixed in high concentration due to superior solubility and storage stability, and it is easily mixed, but it also has superior melanin formation inhibiting effects and superior pigment deposition inhibiting effects, thus freckle and fleck fading effects. It is also safe and without negative effects on skin.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of whitening skin, the method comprising the step of applying a composition comprising a 5,15-diacetyl-3-benzoyllathyrol compound of Formula 1 to human skin:

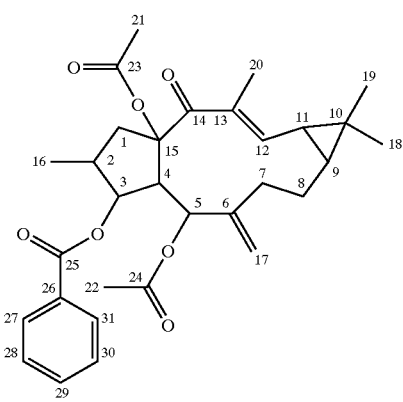

2. The method of claim 1, wherein the compound of Formula 1 is present in an amount of 0.00001% by weight (wt. %) to 10.0 wt. %.

3. The method of claim 2, wherein the compound of Formula 1 is present in an amount of 0.001 wt. % to 1.0 wt. %.

4. A method of whitening skin, the method comprising the step of applying a composition comprising a 5,15-diacetyl-3-benzoyllathyrol compound of Formula 1:

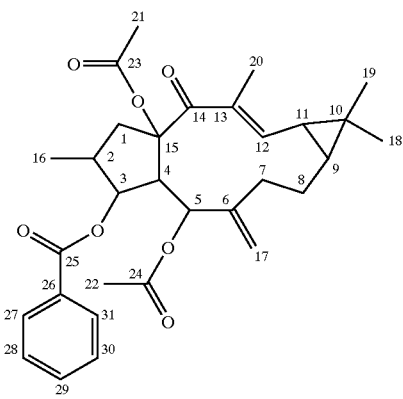

the compound being present in the composition in an amount effective to whiten human skin.

5. The method of claim 4, wherein the compound of Formula 1 is present in an amount of 0.00001 wt. % to 10.0 wt. %.

6. The method of claim 5, wherein the compound of Formula 1 is present in an amount of 0.001 wt. % to 1.0 wt. %.

7. A method of inhibiting melanin formation, the method comprising the step of applying a composition comprising a purified 5,15-diacetyl-3-benzoyllathyrol compound of Formula 1 to human skin:

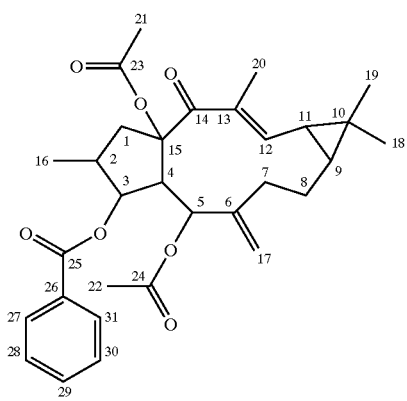

8. The method of claim 7, wherein the compound of Formula 1 is present in amount of 0.00001 wt. % to 10.0 wt. %.

9. The method of claim 8, wherein the compound of Formula 1 is present in an amount of 0.001 wt. % to 1.0 wt. %.

10. A method of inhibiting melanin formation, the method comprising the step of applying a composition comprising a purified 5,15-diacetyl-3-benzoyllathyrol compound of Formula 1:

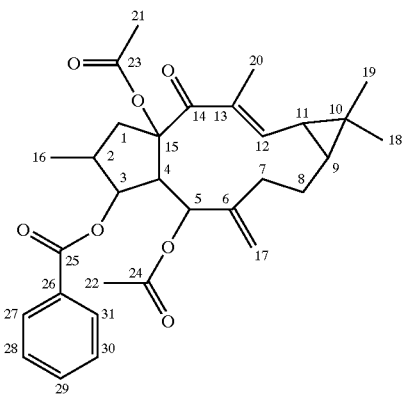

the compound being present in the composition in an amount effective to inhibit melanin formation human skin.

11. The method of claim 10, wherein the compound of Formula 1 is preset in an amount of 0.00001 wt. % to 10.0 wt. %.

12. The method of claim 11, wherein the compound of Formula 1 is present in an amount of 0.001 wt. % to 1.0 wt. %.

* * * * *